United States Patent [19]

Krapcho

[11] 3,953,469
[45] Apr. 27, 1976

[54] BENZOXOZEPINE CARBOXAMIDES AND DERIVATIVES THEREOF

[75] Inventor: John Krapcho, Somerset, N.J.

[73] Assignee: E. R. Squibb & Sons, Inc., Princeton, N.J.

[22] Filed: Aug. 31, 1971

[21] Appl. No.: 176,750

Related U.S. Application Data

[60] Continuation of Ser. No. 723,892, April 24, 1968, abandoned, which is a division of Ser. No. 435,677, Feb. 26, 1965, Pat. No. 3,395,150.

[52] U.S. Cl.............................. 260/333; 260/243 B; 260/244 R; 260/246 R; 260/247.1 L; 260/247.2 A; 260/268 BC; 260/293.57; 260/293,58; 260/294;8 C; 260/295 K; 260/326.35; 269/326.36; 260/332.2 A; 260/347.2; 260/347;3

[51] Int. Cl.² .............. C07D 265/36; C07D 273/00; C07D 413/12; C07D 413/14

[58] Field of Search ........ 260/243 B, 244 R, 246 R, 260/247.1 L, 247.2 A, 268 BC, 293.57, 293.58, 294.8 C, 295 K, 326.35, 326.36, 332.2 A, 347.2, 347.3

[56] References Cited
UNITED STATES PATENTS 2,947,744  8/1960  Lowie.................................. 260/243

Primary Examiner—Alton D. Rollins
Attorney, Agent, or Firm—Lawrence S. Levinson; Merle J. Smith; Stephen B. Davis

[57] ABSTRACT

Compounds of the following formula and their pharmaceutically acceptable acid addition salts

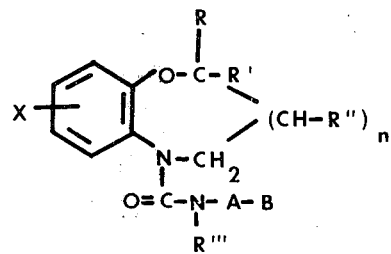

wherein X is hydrogen, lower alkyl, lower alkoxy, lower alkyl mercapto, nitro, di(lower alkyl)amino, halo, or trifluoromethyl; R, R', R'', and R''' are each hydrogen, lower alkyl, cyclopropyl, X-substituted phenyl, furyl, thienyl, or pyridyl, $n$ is zero, one or two, A is lower alkylene and B is a basic nitrogen containing radical of less than 12 carbon atoms are therapeutically active substances which are useful as tranquilizers.

10 Claims, No Drawings

BENZOXOZEPINE CARBOXAMIDES AND DERIVATIVES THEREOF

This is a continuation of application Ser. No. 723,892, filed Apr. 24, 1968, now abandoned, which was a division of application Ser. No. 435,677, filed Feb. 26, 1965, now U.S. Pat. No. 3,395,150.

This invention relates to new chemical compounds having valuable properties and processes for the preparation thereof.

The therapeutically active compounds of this invention are bases of the formula (I):

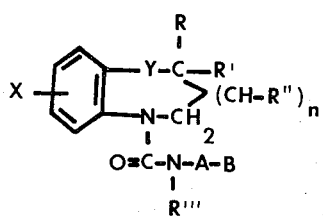

and acid-addition salts thereof, wherein X is hydrogen, lower alkyl, lower alkoxy, lower alkyl mercapto, nitro, di(lower alkyl)amino, halo or trifluoromethyl; R, R', R'', and R''' are each hydrogen, lower alkyl, cycloalkyl, X-substituted phenyl, furyl, thienyl, or pyridyl; Y is methylene, ethylene, or oxy (—O—); n is zero, one or two; A is lower alkylene (preferably ethylene and propylene); and B is a basic nitrogen-containing radical of less than 12 carbon atoms. Among the suitable radicals represented by the symbol B are: amino; (lower alkyl)amino (e.g., methylamino); di(lower alkyl)amino (e.g., diethylamino, dimethylamino, and N-methyl-N-propylamino); (hydroxy-lower alkyl)amino; di(hydroxy-lower alkyl)amino; phenyl(lower alkyl)amino (e.g., benzylamino); N-(lower alkyl)phenyl (lower alkyl)amino; and saturated 5- to 6-membered monocyclic heterocyclic radicals of less than 12 carbon atoms, as exemplified by piperidino; (lower alkyl)piperidino; di(lower alkyl)piperidino; (lower alkoxy)piperidino, 2, 3 or 4-piperidyl; 2, 3 or 4-(N-lower alkyl)piperidyl; homopiperidino; pyrrolidino; (lower alkyl)pyrrolidino; di(lower alkyl)pyrrolidino; (lower alkoxy)pyrrolidino; 2 or 3-pyrrolidyl; 2 or 3-(N-lower alkyl-pyrrolidyl); morpholino; (lower alkyl)morpholino; di(lower alkyl)morpholino; (lower alkoxy)morpholino; thiamorpholino; (lower alkyl)thiamorpholino; di(lower alkyl)thiamorpholino; (lower alkoxy)thiamorpholino; piperazino; homopiperazino; (lower alkyl)piperazino (e.g., $N^4$-methylpiperazino); di(lower alkyl)piperazino; (lower alkoxy)piperazino; hydroxy-lower alkyl-piperazino[e.g., $N^4$-(2-hydroxyethyl)piperazino]; lower alkanoyloxy-lower alkyl-piperazino [e.g., $N^4$-(2-acetoxyethyl)piperazino]; X-substituted phenyl piperazino [e.g., $N^4$-(o-methoxyphenyl)piperazino]; X-substituted phenyl(lower alkyl)piperazino (e.g., $N^4$-phenethylpiperazino); X-substituted cinnamyl(lower alkyl)piperazino; and $N^4$-pyridyl piperazino [e.g., $N^4$-(2-pyridyl)piperazino]. The terms "lower alkyl,", "lower alkoxy,", "lower alkylene," and "lower alkanoyl," as employed herein, include both straight and branched chain radicals of less than eight carbon atoms. The preferred compounds are those wherein X is hydrogen or halo, R is hydrogen, lower alkyl or phenyl, R' and R'' are hydrogen, and R''' is hydrogen or lower alkyl. Particularly preferred are those compounds wherein X is hydrogen or chloro, R is phenyl, Y is methylene, R' and R'' are hydrogen, R''' is lower alkyl (preferably methyl), n is one, A is ethylene or propylene, and B is di(lower alkyl)amino.

As to salts, those coming within the purview of this invention include the acid-addition salts, particularly the non-toxic acid-addition salts. Acids useful for preparing these acid-addition salts include, inter alia, inorganic acids, such as the hydrohalic acids (e.g., hydrochloric and hydrobromic acid), sulfuric acid, nitric acid, boric acid and phosphoric acid, and organic acids, such as maleic, methane sulfonic, cyclohexane sulfamic, tartaric, citric, acetic and succinic acid, theophylline and 8-chlorotheophylline.

The compounds of this invention, including the acid-addition salts thereof, are therapeutically active substances which are useful as tranquilizers and thus can be administered perorally, for example, in the same manner as Chlordiazepoxide in the treatment of irrational fears, anxiety and tension, the dosage for such treatment being adjusted for the activity of the particular compound employed.

The compounds of this invention can be prepared by condensing a compound of the formula (II):

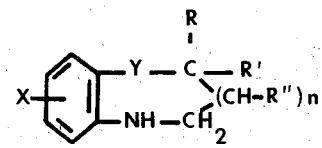

wherein X, R', R'', Y, and n are as hereinbefore defined, with a carbonyl halide, such as phosgene, to yield new intermediates of this invention of the formula (III):

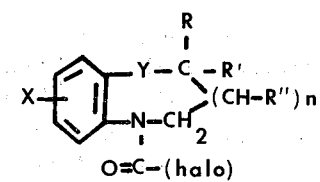

The resulting carbonyl halide of the formula III is then reacted with a diamine of the formula:

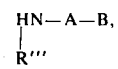

wherein R''', A and B are as hereinbefore defined, to yield the final products of this invention. The free bases can be converted to their acid-addition salts in the usual manner by reaction with the desired acid.

The following examples illustrate the invention (all temperatures being in centigrade):

EXAMPLE 1

N̲-(2-Dimethylaminoethyl)-2,3,4,5-tetrahydro-N̲-methyl-2-phenyl-1,5-benzothiazepine-5-carboxamide, Hydrochloride

A. Preparation of 2,3,4,5-Tetrahydro-2-phenyl-1,5-benzothiazepine

A slurry of 24 g. of lithium aluminum hydride in 950 ml. of dry tetrahydrofuran is treated portionwise with 140 g. of finely-divided 2,3-dihydro-2-phenyl-1,5-benzothiazepin-4-one. The reaction is exothermic and the mixture is allowed to reflux during the addition. After stirring for 2 hours at room temperature, the mixture is refluxed for 3 hours, cooled and treated dropwise with 30 ml. of water and then a solution of 16 g. of sodium hydroxide in 100 ml. of water. The organic phase is filtered from the inorganic salt, washed with ether and the filtrate dried over magnesium sulfate. After evaporation of the solvent, the residue is fractionated to give 118.5 g. of liquid, b.p. 179°–181° (0.2 mm). The distillate slowly crystallized to a yellow solid, m.p. 62°–64°. A sample crystallized from isopropyl ether gave a granular colorless product, m.p. 65°–67°.

B. Preparation of 2,3,4,5-Tetrahydro-2-phenyl-1,5-benzothiazepine-5-carbonyl choride A solution of 44 g. of material from part (A) in 250 ml. of chloroform is stirred and maintained at 15° during the addition of a cold solution of 25.5 g. of phosgene in 300 ml. of toluene. A precipitate separates from the mixture after 1 hour. After standing overnight at room temperature the mixture is slowly heated to reflux over a period of 3 hours and then refluxed for 1 hour. About 250 ml. of solvent is distilled and the residue is cooled to room temperature (410 ml.).

After standing for several days at room temperature, the product begins to crystallize from the solution. A small sample is triturated with toluene and hexane, m.p. about 137°–139°.

C. Preparation of N-[2-(Dimethylamino)ethyl]-2,3,4,5-tetrahydro-N-methyl-2-phenyl-1,5-benzothiazepine-5-carboxamide A solution of the carbonyl chloride obtained in part (B) (205 ml., about 0.09 mole) is diluted wih 200 ml. of chloroform and the resulting solution cooled and maintained at 15°–17° during the dropwise addition of 9.3 g. of N,N,N'-trimethylethylenediamine. The solution is allowed to stir at room temperature for 1 hour and then refluxed for 1 hour. A crystalline solid separates during the heating period. The mixture is cooled, treated with 200 ml. of water containing 5 ml. of conc. hydrochloric acid and diluted with 300 ml. of ether. The mixture is shaken and the aqueous phase is separated, cooled and treated with a cold solution of 10 g. of sodium hydroxide in 50 ml. of water. The crystalline base which separates is extracted with 200 ml. of ether (three times). The three phases are combined, washed with 50 ml. of water and dried over magnesium sulfate. Evaporation of the solvent gives about 22 g. of residue. The latter is crystallized from 120 ml. of hexane to give about 15.7 g. of colorless base, m.p. about 66°–68°.

D. Preparation of N-[2-(Dimethylamino)ethyl]-2,3,4,5-tetrahydro-N-methyl-2-phenyl-1,5-benzothiazepine-5-carboxamide, Hydrochloride A solution of 15.4 g. of the material obtained in part (C) in 700 ml. of ether is treated with a slight excess of ethereal hydrogen chloride to give about 16.3 g. of colorless solid, m.p. about 250°–252°. Crystallization from 170 ml. of absolute alcohol gives about 15.8 g. of colorless solid, m.p. about 240°–250°. The decrease in melting point is probably due to solvation. The latter is dissolved in 200 ml. of hot chloroform, cooled to about 40° and diluted with 400 ml. of ether. The product crystallizes from this solution; yield about 15.5 g., m.p. about 251°–253°.

EXAMPLE 2

N̲-(2-Dimethylaminoethyl)-2,3,4,5-tetrahydro-2-phenyl-1,5-benzothiazepine-5-carboxamide Hydrochloride By substituting 8.0 g. of 2-dimethylaminoethylamine for the N,N,N'-trimethylethylenediamine in part (C) of Example 1, there is obtained 19.0 g. of product; m.p. about 90°–95°. After crystallization from ethyl acetate, the colorless solid melts at about 145°–149°. This material is then crystallized from butanone; m.p. about 151°–153°.

EXAMPLE 3

N-(3-Dimethylaminopropyl)-2,3,4,5-tetrahydro-N-methyl-2-phenyl-1,5-benzothiazepin-5carboxamide Hydrochloride

A. Preparation of N-(3-Dimethylaminopropyl)-2,3,4,5-tetrahydro-N-methyl-2-phenyl-1,5-benzothiazepin-5-carboxamide Interaction of a solution containing 0.12 mole of the carbonyl chloride, prepared in part (B) of Example 1, with 18.3 g. of N,N,N'-trimethyl-1,3-propanediamine by the procedure in part (C) of Example 1, gives about 33.3 g. of residue. The latter is crystallized from 100 ml. of hexane to give about 28.2 g. of colorless base, m.p. about 63°–66°.

B. Preparation of the Hydrochloride Salt

A solution of 28.2 g. of the material obtained in part (A) of this Example in 800 ml. of ether is treated with a slight excess of ethereal hydrogen chloride to give about 30.8 g. of colorless solid, m.p. about 220°–222°. After crystallization from 600 ml. of acetonitrile, the colorless product weighs about 27.0 g., m.p. about 221°–223°.

EXAMPLE 4

N-(2-Dimethylaminoethyl)-2,3,4,5-tetrahydro-N-methyl-2phenyl-1,5-benzoxazepine-5-carboxamide Hydrochloride By substituting an equivalent amount of 2,3-dihydro-2-phenyl-1,5-benzoxazepin-4-(5H)-one, m.p. 123°–125°, (prepared as described in Example 1 of U.S. patent application, Ser. No. 328,048, filed Dec. 4, 1963 now U.S. Pat. No. 3,309,361), for the 2,3-dihydro-2-phenyl-1,5-benzothiazepin-4-one in part (A) of Example 1, and carrying out the procedure of the Example, there is obtained N-(2-dimethylaminoethyl)-2,3,4,5-tetrahydro-N-methyl-2-phenyl-1,5-benzoxazepine-5-carboxamide hydrochloride

EXAMPLE 5

N-(2-Dimethylaminoethyl)-2,3,4,5-tetrahydro-N-methyl-4-phenyl-1-benzazepine-1-carboxamide Hydrochloride By substituting an equivalent amount of 1,3,4,5-tetrahydro-4-phenyl-2H-1-benzazepine-2-one, m.p. 140°–142° (prepared as described in Example 13 of U.S. patent application, Ser. No. 418,910, filed Dec. 16, 1964 now U.S. Pat. No. 3,330,823), for the 2,3-dihydro-2-phenyl-1,5-benzothiazepin-4-one in part (A) of Example 1 carrying out the procedure of the Example, there is obtained N-(2-dimethylaminoethyl)-2,3,4,5-tetrahydro-N-methyl-4-phenyl-1-benzazepine-1-carboxamide hydrochloride.

EXAMPLE 6

N-(2-Dimethylaminoethyl)-1,2,3,4,5,6-hexahydro-N-methyl-4-phenyl-1-benzazocine-1-carboxamide Hydrochloride By substituting an equivalent amount of 3,4,5,6-tetrahydro-4-phenyl-1-benzazocin-2(H)-one, m.p. 188°–189° (prepared as described in Example 1 of U.S. patent application, Ser. No. 418,910, filed Dec. 16, 1964), for the 2,3-dihydro-2-phenyl-1,5-benzothiazepin-4-one in part (A) of Example 1 and carrying out the precedure of the Example, there is obtained N-(2-dimethylaminoethyl)-1,2,3,4,5,6-hexahydro-N-methyl-4-phenyl-benzazocine-1carboxamide hydrochloride.

EXAMPLE 7

N-(2-Dimethylaminoethyl)-3,4-dihydro-2H-N-methyl-2-phenyl-1,4-benzothiazine-4-carboxamide Hydrochloride By substituting an equivalent amount of 3,4-dihydro-2-phenyl-2H-1,4-benzothiazin-3-one for the 2,3-dihydro-2-phenyl-1,5-benzothiazepin-4-one in part (A) of Example 1 and carrying out the procedure of the Example, there is obtained N-(2-dimethylaminoethyl)-3,4-dihydro-2H-N-methyl-2-phenyl-1,4-benzothiazine-4-carboxamide hydrochloride.

EXAMPLE 8

N-(2-Dimethylaminoethyl)-N-methyl-2-phenyl-1,2,3,4,5,6-hexahydro-1,6-benzothiazocine-6-carboxamide Hydrochloride By substituting an equivalent amount of 3,4-dihydro-2-phenyl-2H-1,6-benzothiazocin-5(6H)-one for the 2,3-dihydro-2-phenyl-1,5-benzothiazepin-4-one in part (A) of Example 1 and carrying out the procedure of the Example, there is obtained N-(2-dimethylaminoethyl)-N-methyl-2phenyl-1,2,3,4,5,6-hexahydro-1,6-benzothiazocine-6-carboxamide hydrochloride.

Similarly, by substituting the following reactants for the 2,3-dihydro-2-phenyl-1,5-benzothiazepin-4-one in part (A) of Example 1 and carrying out the procedure of the Example, there is obtained the indicated N-(2-dimethylaminoethyl)-N-methyl product in the form of its hydrochloride salt:

| Example | Reactant | Product |
| --- | --- | --- |
| 9 | 4,5-Dihydro-3-phenyl-1-H-1-benzazepin-2(3H)-one | N-(2-Dimethylaminoethyl)-2,3,4,5-tetrahydro-N-methyl-3-phenyl-1-benzazepine-1-carboxamide |
| 10 | 3,4,5,6-Tetrahydro-4-(o-chlorophenyl)-1-benzazocine-2(1H)-one | N-(2-Dimethylaminoethyl)-1,2,3,4,5,6-hexahydro-N-methyl-4-(o-chlorophenyl)-1-benzazocine-1-carboxamide |
| 11 | 3,4,5,6-Tetrahydro-4-o-tolyl-1-benzazocin-2(H)-one | N-(2-Dimethylaminoethyl)-1,2,3,4,5,6-hexahydro-N-methyl-4-o-tolyl-1-benzazocine-1-carboxamide |
| 12 | 4,5-Dihydro-3-o-methoxyphenyl-1H-1-benzazepin-2(3H)-one | N-(2-Dimethylaminoethyl)-2,3,4,5-tetrahydro-N-methyl-3-o-methoxyphenyl-1-benzazepine-1-carboxamide |
| 13 | 4,5-Dihydro-3-(p-methoxyphenyl)-8-methyl-1H-1-benzazepin-2(3H)-one | N-(2-Dimethylaminoethyl)-4,5-dihydro-N-methyl-3-p-methoxyphenyl-8-methyl-1-benzazepine-1-carboxamide |
| 14 | 2-Methyl-2,3-dihydro-1,5-benzoxazepine-4-one | N-(2-Dimethylaminoethyl)-2,3,4,5-tetrahydro-N,2-dimethyl-1,5-benzoxazepine-5-carboxamide |
| 15 | 2,3-Dihydro-2-(p-methoxyphenyl)-1,5-benzoxazepin-4-one | N-(2-Dimethylaminoethyl)-2,3,4,5-tetrahydro-N-methyl-2-(p-methoxyphenyl)-1,5-benzoxazepine-5-carboxamide |
| 16 | 2,3-Dihydro-1,5-benzoxazepin-4-one | N-(2-Dimethylaminoethyl)-2,3,4,5-tetrahydro-N-methyl-1,5-benzoxazepine-5-carboxamide |
| 17 | 2,3-Dihydro-2-benzyl-1,5-benzoxazepin-4-one | N-(2-Dimethylaminoethyl)-2,3,4,5-tetrahydro-N-methyl-2-benzyl-1,5-benzoxazepine-5-carboxamide |
| 18 | 2,3-Dihydro-2-(α-furyl)-1,5-benzoxazepin-4-one | N-(2-Dimethylaminoethyl)-2,3,4,5-tetrahydro-N-methyl-2-(α-furyl)-1,5-benzoxazepine-5-carboxamide |
| 19 | 7-Chloro-2,3-dihydro-2-phenyl-1,5-benzoxazepin-4-one | N-(2-Dimethylaminoethyl)-2,3,4,5-tetrahydro-7-chloro-N-methyl-2-phenyl-1,5-benzoxazepine-5-carboxamide |
| 20 | 7-Methyl-2,3-dihydro-2-phenyl-1,5-benzoxazepin-4-one | N-(2-Dimethylaminoethyl)-2,3,4,5-tetrahydro-N,7-dimethyl-2-phenyl-1,5-benzoxazepine-5-carboxamide |

-continued

| Example | Reactant | Product |
|---|---|---|
| 21 | 7-Methoxy-2,3-dihydro-2-phenyl-1,5-benzoxazepin-4-one | N-(2-Dimethylaminoethyl)-2,3,4,5-tetrahydro-7-methoxy-N-methyl-2-phenyl-1,5-benzoxazepine-5-carboxamide |
| 22 | 7-(Trifluoromethyl)-2,3-dihydro-2-phenyl-1,5-benzoxazepin-4-one | N-(2-Dimethylaminoethyl)-2,3,4,5-tetrahydro-N-methyl-7-(trifluoromethyl)-2-phenyl-1,5-benzoxazepine-5-carboxamide |
| 23 | 7-(methylmercapto)-2,3-dihydro-1,5-benzothiazepin-4-one | N-(2-Dimethylaminoethyl)-2,3,4,5-tetrahydro-N-methyl-7-(methylmercapto)-1,5-benzothiazepine-5-carboxamide |

Similarly, by substituting other diamines for the N,N,N'-trimethylethylenediamine in part (C) of Example 1 and carrying out the remaining steps in the procedure, the indicated N-Z-N-Z'-2,3,4,5-tetrahydro-2-phenyl-1,5-benzothiazepine-5-carboxamide hydrochloride is obtained:

| | | Product | |
|---|---|---|---|
| Example | Reactant | Z is: | Z' is: |
| 24 | 2-Pyrrolidinoethylamine | 2-Pyrrolidinoethyl | Hydrogen |
| 25 | N,N'-Dimethyl-N-phenethyl-ethylenediamine | 2-(N-Methyl-N-phenethylamino)-ethyl | Methyl |
| 26 | 2-Morpholinoethylamine | 2-Morpholinoethyl | Hydrogen |
| 27 | N-(2-piperidinoethyl)-N-methylamine | 2-Piperidinoethyl | Methyl |
| 28 | N',N-Dimethyl-N-cyclopropylethylenediamine | 2-(N-Methyl-N-cyclopropylamino)-ethyl | Methyl |
| 29 | N-Methyl-2-(4-methylpiperazino)ethylamine | 2-(4-Methylpiperazino)ethyl | Methyl |
| 30 | N-Ethyl-2-[4-(o-ethylthiophenyl)piperazino]ethylamine | 2-[4-(o-Ethylthiophenyl)piperazino]-ethyl | Ethyl |
| 31 | N-Methyl-2-[4-(phenethyl)-piperazino]ethylamine | 2-[4-(phenethyl)-piperazino]ethyl | Methyl |
| 32 | N-Isopropyl-3-[4-(2-pyridyl)piperazino]propylamine | 3-[4-(2-Pyridyl)-piperazino]propyl | Isopropyl |
| 33 | N-Cyclopropyl-3-(4-cinnamylpiperazino)-propylamine | 3-(4-Cinnamyl)-piperazino)propyl | Cyclopropyl |

The invention may be variously otherwise embodied within the scope of the appended claims.

What is claimed is:

1. A compound selected from the group consisting of bases of the formula:

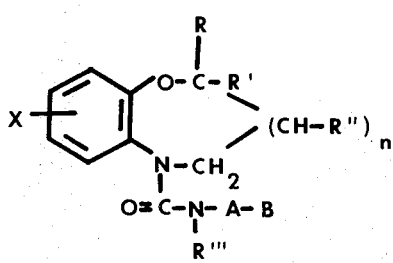

and pharmaceutically acceptable acid-addition salts thereof, wherein X is selected from the group consisting of hydrogen, lower alkyl, lower alkoxy, lower alkyl mercapto, nitro, di(lower alkyl)amino, halo and trifluoromethyl; R, R', R'' and R''', are each selected from the group consisting of hydrogen, lower alkyl, cyclopropyl, X-substituted phenyl, furyl, thienyl and pyridyl; $n$ is selected from the group consisting of zero, one and two; A is lower alkylene and B is basic nitrogen-containing radical of less than 12 carbon atoms selected from the group consisting of amino; (lower alkyl)amino; (hydroxy-lower alkyl)amino; di(hydroxy-lower alkyl)amino di(lower alkyl)amino; phenyl (lower alkyl)amino; N-(lower alkyl)phenyl-(lower alkyl)amino; piperidino; (lower alkyl)piperidino; di(lower alkyl)piperidino; (lower alkoxy)piperidino 4-(N-lower alkyl)-piperidyl; homopiperidino; pyrrolidino; (lower alkyl)pyrrolidino; di(lower alkyl)pyrrolidino; (lower alkoxy)pyrrolidino; morpholino; (lower alkyl)morpholino; di(lower alkyl)morpholino; (lower alkoxy)-morpholino; thiamorpholino; (lower alkyl)thiamorpholino; di(lower alkyl)thiamorpholino; (lower alkoxy)thiamorpholino; piperazino; homopiperazino; (lower alkyl)piperazino; di(lower alkyl)piperazino; (lower alkoxy)piperazino; hydroxy-lower alkylpiperazino; lower alkanoyloxy-lower alkyl-piperazino; X-substituted phenylpiperazino; X-substituted phenyl(lower alkyl)piperazino; X-substituted cinnamyl (lower alkyl)-piperazino and $N^4$-pyridyl piperazino and pharmaceutically acceptable salts thereof.

2. A compound in accordance with claim 1 having the name N-(2-dimethylaminoethyl)-2,3,4,5-tetrahydro-N,2-dimethyl-1,5-benzoxazepine-5-carboxamide.

3. A compound in accordance with claim 1 having the name N-(2-dimethylaminoethyl)-2,3,4,5-tetrahydro-N-methyl-2-(p-methoxyphenyl)-1,5-benzozoxazepine-5-carboxamide.

4. A compound in accordance with claim 1 having the name N-(2-dimethylaminoethyl)-2,3,4,5-tetrahydro-N-methyl-1,5benzoxazepine-5-carboxamide.

5. A compound having the name N-(2-dimethylaminoethyl)-2,3,4,5,-tetrahydro-N-methyl-2-benzyl-1,5-benzoxazepine-5-carboxamide.

6. A compound in accordance with claim 1 having the name N-(2-dimethylaminoethyl)-2,3,4,5-tetrahydro-N-methyl-2-(α-furyl)-1,5-benzoxazepine-5-carboxamide.

7. A compound in accordance with claim 1 having the name N-(2-dimethylaminoethyl)-2,3,4,5-tetrahydro-7-chloro-N-methyl-2-phenyl-1,5-benzoxazepine-5-carboxamide.

8. A compound in accordance with claim 1 having the name N-(2-dimethylaminoethyl)-2,3,4,5-tetrahydro-N,7-dimethyl-2-phenyl-1,5-benzoxazepine-5-carboxamide.

9. A compound in accordance with claim 1 having the name N-(2-dimethylaminoethyl)-2,3,4,5-tetrahydro-7-methoxy-N-methyl-2-phenyl-1,5-benzoxazepine-5-carboxamide.

10. A compound in accordance with claim 1 having the name N-(2-dimethylaminoethyl)-2,3,4,5-tetrahydro-N-methyl-7-(trifluoromethyl)-2-phenyl-1,5-benzoxazepine-5-carboxamide.

* * * * *

UNITED STATES PATENT AND TRADEMARK OFFICE
CERTIFICATE OF CORRECTION

PATENT NO. : 3,953,469
DATED : 4/27/76
INVENTOR(S) : John Krapcho

It is certified that error appears in the above-identified patent and that said Letters Patent are hereby corrected as shown below:

In the title, "Benzoxozepine" should read --Benzoxazepine--.

Col. 3, line 29, "choride" should read --chloride--.

Col. 4, line 32, "5carboxamide" should read --5-carboxamide--.

Col. 4, line 57, "2phenyl" should read --2-phenyl--.

Col. 5, line 28, "precedure" should read --procedure--.

Col. 8, lines 50 and 51, "(hydroxy-lower alkyl)amino; di(hydroxy-lower alkyl)amino di-(lower alkyl)amino;" should read --di(lower alkyl)amino; (hydroxy-lower alkyl)-amino; di(hydroxy-lower alkyl)amino;--.

Col. 9, line 10, "1,5benzoxazepine" should read --1,5-benzoxazepine--.

Signed and Sealed this

Twenty-first Day of September 1976

[SEAL]

Attest:

RUTH C. MASON
Attesting Officer

C. MARSHALL DANN
Commissioner of Patents and Trademarks